United States Patent [19]

Näf et al.

[11] 4,374,051
[45] Feb. 15, 1983

[54] UTILIZATION OF NITROGEN CONTAINING HETEROCYCLIC DERIVATIVES AS PERFUME INGREDIENTS

[75] Inventors: Regula Näf, Geneva; Wilhelm Pickenhagen, Chavannes-des-Bois; Anthony F. Morris, Gingins, all of Switzerland

[73] Assignee: Firmenich SA, Geneva, Switzerland

[21] Appl. No.: 228,357

[22] Filed: Jan. 26, 1981

[30] Foreign Application Priority Data

Feb. 6, 1980 [CH] Switzerland ............................ 934/80

[51] Int. Cl.$^3$ ................................................ A61K 7/46
[52] U.S. Cl. ................................ 252/522 R; 546/314; 546/348; 546/352
[58] Field of Search .................... 252/522 R; 546/314, 546/348, 352

[56] References Cited

U.S. PATENT DOCUMENTS

| | | |
|---|---|---|
| 3,669,908 | 6/1972 | Hall ................................. 252/522 R |
| 3,716,543 | 2/1973 | Hall .................................... 546/350 |
| 4,005,227 | 1/1977 | Winter et al. ........................ 546/348 |
| 4,018,910 | 4/1977 | Winter et al. ........................ 546/314 |

OTHER PUBLICATIONS

Arctander, S., *Perfume and Flower Chemicals*, vols. I and II, Published by Author Montclair, N.J., (1969), Minographs 499, 2776 and 2126.

*Primary Examiner*—John F. Niebling
*Attorney, Agent, or Firm*—Pennie & Edmonds

[57] ABSTRACT

Certain pyridine derivatives have been found to possess particularly useful odorous properties. They develop green and herbaceous fragrance notes and have a specific utility for the reconstitution of the essential oil of *Artemesia Vulgaris*.

3 Claims, No Drawings

UTILIZATION OF NITROGEN CONTAINING HETEROCYCLIC DERIVATIVES AS PERFUME INGREDIENTS

SUMMARY OF THE INVENTION

The instant invention relates to the field of perfumery. In particular it discloses a method for improving, enhancing or modifying the odorous properties of perfumes, perfume bases or perfume articles, which comprises the step of adding thereto at least one of the pyridine derivatives belonging to the following class:
a. 2-isopropenyl-pyridine,
b. 3-isopropenyl-pyridine,
c. 2-isopropyl-5-methyl-pyridine,
d. 2-methyl-5-isopropenyl-pyridine,
e. 2-isopropyl-5-acetyl-pyridine,
f. 2-methyl-5-acetyl-pyridine and
g. 2-methyl-5-isopropyl-pyridine.

The present invention also provides a perfume composition containing as perfuming effective ingredient at least one of the pyridine derivatives a. to g. mentioned above. In particular, this invention relates to a perfume composition of Artemesia Vulgaris type containing as perfuming effective ingredient at least one of the pyridine derivatives a. to g. mentioned above.

Finally, the invention relates to 2-isopropyl-5-acetyl-pyridine as new composition of matter.

BACKGROUND OF THE INVENTION

Certain nitrogen-containing heterocyclic compounds are utilized to a limited extent by the perfume industry. Among them, one may cite particularly some pyrazine derivatives, namely alkyl- or alkoxy-pyrazines [see e.g.: DE-OS No. 20 280977]. To date however, pyridine derivatives have not been recognized in the art as having any particular utility since their very powerful acrid and pungent odor did not appear to be compatible with the current perfume compositions.

We have now discovered that compounds a. to g. mentioned above develop very interesting fragrance properties at high dilutions. One aspect which should be emphasized is the absence, in the spectrum of their odorous features, of the typical unpleasant character of pyridine. They develop, in fact, green and herbaceous notes reminiscent of certain aspects of petitgrain oil or even tobacco. Due to their properties, the pyridine compounds of the invention find a wide range of utility; typically however, they can be used for the reconstitution of essential oils, especially Artemesia Vulgaris oil, a composition which is highly prized in perfumery for its use to add freshness and warmth to compositions such as lavender-colognes, chypre or fougere.

PREFERRED EMBODIMENTS OF THE INVENTION

Pyridine compounds a. to g. can be used in their isolated form or more frequently in admixture with other perfume coingredients in solution with current solvents such as alcohols or diethyl-phthalate, or in combination with a carrier or a support.

When compounds a. to g. are used in accordance with the invention, for example as ingredients for the manufacture of perfume compositions, interesting olfactive effects can be achieved by the use of very low concentrations. Due to their strength, concentrations on the order of between about 10 to about 100 ppm (parts per million), based on the total weight of the composition into which they are incorporated, can advantageously achieve interesting results. Among the compounds of the invention, 2-isopropyl-5-acetyl-pyridine and 2-methyl-5-isopropenyl-pyridine are preferred.

Compounds a. to g. also possess a utility for the flavor industry. For instance, 2-isopropenyl-pyridine develops a green, earthy and vegetable gustative note.

With the exception of 2-isopropyl-5-acetyl-pyridine, the compounds of the invention are known chemical entities.

Hereinbelow we shall indicate for each one of the said compounds a literature reference describing the respective method of preparation.
a. 2-Isopropenyl-pyridine: Ber. 40, 1328 (1907);
b. 3-isopropenyl-pyridine: Chemisches Zentrablatt 1926, I 3336;
c. 2-isopropyl-5-methyl-pyridine: Ber. 60, 1719 (1927);
d. 2-methyl-5-isopropenyl-pyridine: Chem. Abstr. 83, 28057 m (1975);
e. 2-isopropyl-5-acetyl-pyridine: new compound (see below);
f. 2-methyl-5-acetyl-pyridine: Ber. 28, 1765 (1895);
g. 2-methyl-5-isopropyl-pyridine: Chemisches Zentralblatt 1930, I 3556.

Compounds a. to d. f. and g. used in accordance with the invention showed the following analytical data:
a. NMR: 2.25 (3H, s); 5.3 (1H, t, J=1 Hz); 5.7 (1H, s); 7.3 and 8.6 (3H, m)δppm;
MS: m/e=118(100), 119(77), 79(30), 52(17), 104(13), 58.5(11), 93(10), 39(9).
b. NMR: 2.1 (3H, s); 5.15 (1H, s); 5.4 (1H, s); 7.2, 7.7 and 8.6 (3H, m)δppm;
MS: m/e=119(100), 118(56), 104(36), 91(20), 51(18), 39(14), 77(11), 65(6), 58.5(5).
c. MS: e/e=120(100), 134(38), 107(34), 106(33), 135 (26), 93(20), 65(16), 39(14).
d. NMR: 2.07 (3H, s); 2.56 (3H, s); 5.26 (1H, s); 5.39 (1H, s); 7.06, 7.65 and 8.6 (3H, m)δppm;
MS: m/e=133(100), 118(51), 91(27), 132(23), 117(22), 39(20), 65(17), 51(12), 77(8).
f. NMR: 2.6 (6H, 2s); 7.2, 8.1 and 9.0 (3H, m)δppm;
MS: m/e=120(100), 92(86), 65(41), 135(40), 43(20), 39(19).
g. MS: m/e=120(100), 135(31), 77(9), 92(8), 39(6), 65(5).

Preparation of 2-isopropyl-5-acetyl-pyridine (compound e.)

17.5 ml of a 1.5 N solution of butyl-lithium in hexane were added dropwise at 0°/−10° to a solution of 2.75 g (27.5 mmole) of diisopropylamine in 15 ml of anhydrous tetrahydrofurane (THF). A solution of 680 mg (5.03 mmole) of 2-methyl-5-acetyl-pyridine in 7 ml of THF was subsequently added thereto, followed by a solution of 4.25 g (29.9 mmole) of methyl iodide in 10 ml of anhydrous THF. The temperature of the reaction mixture rose to about 15°. After cooling to 0°, the mixture was left standing for 30 minutes, then it was poured onto crushed ice and extracted with ether. After evaporation of the volatiles under reduced pressure, the desired product was obtained by fractional distillation: b. p. 125°/10 Torr; 550 mg (yield 67%).

NMR (60 MHz): 1.33 (6H, d, J=7 Hz); 2.60 (3H, s); 3.20 (1H, q, J=7 Hz); 7.22 (1H, m); 8.12 (1H, m); 9.05 (1H, broad s)δppm;
MS: m/e=163(3), 162(38), 161(42), 149(11), 148(100), 135(30).

The temperature values given above are indicated in degrees centigrade.

The invention is further illustrated by the following examples.

EXAMPLE 1

Perfume composition

A base perfume composition was prepared by admixing the following ingredients (parts by weight):

|  |  |
|---|---|
| Camphene | 85 |
| Camphor | 170 |
| Eucalyptol | 85 |
| Linalol | 330 |
| Plicatone* | 330 |
| Total | 1000 |

*Origin: Firmenich SA, Geneva: see DE-PS 22 49376 = (5-methyl-tricyclo[6.2.1.0$^{2,7}$]undecan-4-one)

By adding to the above base 2-isopropyl-5-acetyl-pyridine in a concentration of 80 ppm, we obtained a novel composition having a marked herbaceous character which was reminiscent of the odorous note presented by the oil of Artemesia Vulgaris, aspic, lavandin or clarysage.

EXAMPLE 2

Perfume composition

A base perfume composition was prepared by admixing the following ingredients (parts by weight):

|  |  |
|---|---|
| Geranyl acetate | 200 |
| cis-Hex-3-enol 1%* | 120 |
| cis-Hex-3-enyl-butyrate 1%* | 120 |
| Synthetic linalol | 7360 |
| Synthetic linalyl acetate | 1800 |
| Terpenyl acetate | 200 |
| Terpineol | 100 |
| Total | 9900 |

*in diethyl phtalate

The addition to the above composition of 100 parts by weight of a solution at 1% of 2-methyl-5-isopropenyl-pyridine promoted the softening of the chemical odorous character conferred by the esters present. The resulting novel composition presented an elegant, bergamot like, clary-sage like fragrance with slightly green and herbal tones.

What we claim is:

1. A method for improving, enhancing or modifying the odorous properties of perfumes, perfume bases or perfumed articles which comprises the step of adding thereto at least one of the pyridine derivatives selected from the group consisting of:
   a. 2-isopropenyl-pyridine,
   b. 3-isopropenyl-pyridine,
   c. 2-isopropyl-5-methyl-pyridine,
   d. 2-methyl-5-isopropenyl-pyridine,
   e. 2-isopropyl-5-acetyl-pyridine,
   f. 2-methyl-5-acetyl-pyridine, and
   g. 2-methyl-5-isopropyl-pyridine,
wherein the concentration of the pyridine derivative is between about 10 to about 100 ppm of the total weight of the perfume, perfume base or perfumed article composition.

2. A perfume composition comprising at least one of the pyridine derivatives a. to g. claim 1 as a perfuming effective ingredient.

3. A perfume composition of the *Artemesia Vulgaris* type comprising as a perfuming effective ingredient at least one of the pyridine derivatives a. to g. of claim 1.

* * * * *